United States Patent [19]
Geerlings

[11] Patent Number: 5,457,323
[45] Date of Patent: Oct. 10, 1995

[54] PROCESS FOR STRIPPING RADON-220 FROM RADIOACTIVE ISOTOPE MIXTURE

[75] Inventor: Maurtis W. Geerlings, Rozendaal, Netherlands

[73] Assignee: Akzo Nobel N.V., Arnhem, Netherlands

[21] Appl. No.: 296,071

[22] Filed: Aug. 24, 1994

Related U.S. Application Data

[63] Continuation of Ser. No. 30,502, Mar. 12, 1993, abandoned.
[51] Int. Cl.$^6$ .................................................. G01N 23/00
[52] U.S. Cl. ........................................................ 250/432 PD
[58] Field of Search ...................................... 250/432 PD

[56] References Cited

U.S. PATENT DOCUMENTS

| | | | |
|---|---|---|---|
| 4,975,574 | 12/1990 | Lucas | 250/253 |
| 5,038,046 | 8/1991 | Norman et al. | 250/432 PD |
| 5,235,190 | 8/1993 | Tucker et al. | 250/435 |

FOREIGN PATENT DOCUMENTS 90-15625  12/1990  WIPO.

*Primary Examiner*—Bruce C. Anderson
*Attorney, Agent, or Firm*—Richard P. Fennelly; Louis A. Morris

[57] ABSTRACT

The separation of radon-220 from a liquid radioactive composition comprising radon-220, radium-224, and radium-225, and their daughter isotopes, as well as may be their thorium precursors, which liquid radioactive composition is adapted for use in the ultimate production of actinium-225 for radioimmunotherapy, can be achieved by treating the composition with a gas to strip the radon-220 from the composition.

6 Claims, No Drawings

PROCESS FOR STRIPPING RADON-220 FROM RADIOACTIVE ISOTOPE MIXTURE

This is a continuation of application Ser. No. 08/030,502 filed Mar. 12, 1993, abandoned.

BACKGROUND OF THE INVENTION

It is known from PCT International Application No. WO 90/15625 to conduct radioimmunotherapy using actinium-225, or one of its daughters, as the alpha-particle source in a radioimmunoconjugate which also comprises a chelating agent and a tumorspecific antibody. In addressing some of the disadvantages of previously proposed alpha-particle emitters, this patent application identifies radon-220, a highly radioactive inert (noble) gas from the decay chain of thorium-228 and radium-224, as an undesired by-product of producing bismuth-212, for example. The occurrence of radon-220 in a decay chain requires special shielding and containment facilities if used in a hospital setting for example.

The above-mentioned patent application teaches the use of uranium-233, which is relatively abundantly stockpiled as an unused source of fuel for nuclear breeder reactors. The use of this material as a source for the actinium-225, through its intermediate decay product thorium-229, is said to possess a number of advantages, including the production of no significant amounts of noble gas isotopes, such as radon-220.

Unfortunately, the availability of uranium-233 as a starting material for the manufacture of the desired intermediate product, thorium-229, as a source for the actinium-225 may be quite limited due to governmental security regulations, on the one hand, and a potentially largely increased demand for this material, on the other hand. Hence, there is a need for non-controlled alternative source materials of greater availability.

The use of radium-226 will cope with the availability issue. Its irradiation by neutrons in a nuclear high flux reactor will generate the needed thorium-229. But the co-generation of comparable amounts of thorium-228 causes the occurrence of radon-220 as one of the decay products in this product mix. Both thorium isotopes decay in a relatively large cascade, starting with radium isotope, being radium-225 from thorium-229 and radium-224 from thorium-228. It is the decay train of undesired radium-224 which is responsible for the production of the undesired radon-220.

DESCRIPTION OF THE INVENTION

The present invention provides a convenient way in which to achieve the removal of the undesired radon-220 from a radioactive, liquid composition comprising radon-220, radium-224, and radium-225 which comprises treating the composition with a gas to strip the radon-220 from the composition. In this manner, the use of radium-226 as a feed source for the thorium-229 will be greatly facilitated and the serious problem in regard to the undesired presence of radon-220 in the isotope mixture of radium-224 and radium-225 be minimized.

Upon reading the present description of the result to be achieved in accordance with the present invention, namely, the stripping of the undesired radon-220 from the radioactive isotope mixture, the person of ordinary skill in the art will be able to devise means for accomplishing such a result with relative ease. A wide variety of sparging gases can be used including air or inert gases, such as nitrogen, helium, and the like. The temperature conditions are not critical although ambient temperatures are preferred since cooling and heating are not required with such conditions. The flow rate of gas to be employed will also variable depending upon the rate of radon-220 removal desired.

The foregoing description has been provided to illustrate certain embodiments of the present invention and, for that reason should not be construed in a limiting sense. The scope of protection is set forth in the claims which follow.

I claim:

1. A process for the separation of radon-220 from a liquid radioactive composition comprising radon-220, radium-224, and radium-225, which liquid radioactive composition is derived from the use of radium-226 as a feed source for thorium-229 and which liquid radioactive composition is then used in the ultimate production of actinium-225 for radioimmunotherapy, which separation of radon-220 comprises treating the liquid radioactive composition with a gas to strip the radon-220 therefrom.

2. A process as claimed in claim 1 wherein the gas is air.

3. A process as claimed in claim 1 wherein the treatment is conducted at ambient temperature.

4. A process as claimed in claim 1 where the gas is air and the treatment is conducted at ambient temperature.

5. A process as claimed in claim 1 wherein the gas is an inert gas.

6. A process as claimed in claim 1 where the gas is inert gas and the treatment is conducted at ambient temperature.

* * * * *